(12) United States Patent
Porsch et al.

(10) Patent No.: US 8,481,329 B2
(45) Date of Patent: Jul. 9, 2013

(54) ANALYSIS SYSTEM FOR THE PHOTOMETRIC DETERMINATION OF AN ANALYTE IN A BODY FLUID

(75) Inventors: Ulrich Porsch, Weinheim (DE); Robert Lorenz, Worms (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 459 days.

(21) Appl. No.: 12/606,361

(22) Filed: Oct. 27, 2009

(65) Prior Publication Data
US 2010/0075433 A1 Mar. 25, 2010

(30) Foreign Application Priority Data
Apr. 27, 2007 (EP) .................................. 07008615

(51) Int. Cl.
*G01N 21/00* (2006.01)

(52) U.S. Cl.
USPC .......... 436/164; 436/43; 436/172; 422/82.09; 422/87

(58) Field of Classification Search
None
See application file for complete search history.

(56) References Cited

U.S. PATENT DOCUMENTS

| | | | |
|---|---|---|---|
| 5,352,351 A | 10/1994 | White et al. | |
| 5,780,304 A | 7/1998 | Matzinger et al. | |
| 6,656,742 B2 * | 12/2003 | Blum et al. | 436/172 |
| 6,825,918 B2 | 11/2004 | Eisenmann et al. | |
| 7,154,593 B2 | 12/2006 | Eisenmann et al. | |

FOREIGN PATENT DOCUMENTS

| | | |
|---|---|---|
| DE | 10156809 A1 | 6/2003 |
| EP | 0387630 A2 | 9/1990 |
| EP | 0974303 A1 | 1/2000 |

* cited by examiner

*Primary Examiner* — Robert Xu
(74) *Attorney, Agent, or Firm* — Krieg DeVault LLP

(57) ABSTRACT

The invention relates to an analysis system for the photometric determination of an analyte in a body fluid, having an analysis device and a test carrier. The test carrier has an evaluation zone in which a photometrically detectable change takes place as the result of a reaction of a sample of the body fluid which contacts the test carrier with a reagent contained in the test carrier. The analysis device comprises an optical emitter for emitting light onto the evaluation zone, an optical receiver for receiving light from the evaluation zone and for generating a measurement signal corresponding to the received light, and a measurement and evaluation device with a measuring unit and an evaluating unit. The measurement signal is amplified and digitalized in the measuring unit. In the evaluating unit, the concentration value is determined from the digitalized measurement signal. In the evaluating unit, a control value of a control parameter is detected at one detection point during the processing after the calculation step. An error in the measurement and evaluation device is recognized if the deviation of the control value from the expected value exceeds a predefined threshold value.

16 Claims, 3 Drawing Sheets

ANALYSIS SYSTEM FOR THE PHOTOMETRIC DETERMINATION OF AN ANALYTE IN A BODY FLUID

CLAIM OF PRIORITY

The present application is a continuation application based on and claiming priority to PCT Application No. PCT/EP2008/002782, filed Apr. 9, 2008, which claims priority to European Patent Application 07008615.2, filed Apr. 27, 2007, each of which are hereby incorporated by reference in their entireties.

TECHNICAL FIELD OF THE INVENTION

The present invention relates to an analysis system for the photometric determination of the concentration of an analyte in a body fluid having an analysis instrument and a test carrier. The test carrier has a evaluation zone, in which a photometrically detectable change occurs as the result of a reaction of a sample of the body fluid, which contacts the test carrier, with a reagent contained in the test carrier.

BACKGROUND

Analysis systems for the photometric determination of an analyte in a body fluid, which use disposable test elements, test carriers, or test strips, are known. They are used in order to determine the concentration of various analytes, such as glucose or cholesterol in blood. The test carriers typically have the form of test strips, however, other forms of test elements are common, such as flat, approximately square plates.

The test carriers typically contain reagents, whose reaction with the sample results in a detectable change, which is measured by means of a measuring and evaluation device associated with the system. In particular, photometric analysis systems are common, in which the reaction causes a color change in a detection layer of the test element, which is measured photometrically. The intensity of the light reflected from the test carrier is typically determined for this purpose.

Upon proper use, the photometric analysis systems typically operate reliably. However, if the required care is not applied by the user upon use of the device or the test carrier and/or test strips, flawed measurement values may result.

Nonetheless, flawed measurement results may also occur upon proper use, in particular if fabrication errors exist in the analysis instrument or in the test carrier. Although great care is used in the production of such analysis instruments and test strips, the need exists to determine malfunctions of the measuring device, in order to avoid flawed analysis values. Because, for example, when determining the concentration of the glucose content, the measurement result is used for the therapy of a patient, in particular to determine the dosing of the insulin, an error-free analysis value is particularly important. An incorrect administration of insulin (excessively low or high insulin administration) based on a flawed measurement result can result in physically hazardous and life-threatening situations.

Analysis systems for optical blood sugar measurement are known in the prior art and are dealt with, for example, in the following publications: DE 101 56 809 A1; U.S. Pat. No. 5,780,304; EP 0 974 303 A1; and EP 0 387 630 A2.

It is typically monitored in the photometric analysis system whether the measuring unit operates error-free. On the one hand, it is verified on the basis of reference values whether the test carrier used is sufficiently wetted. On the other hand, the time curve of the measurement value is verified. For example, it is verified as to whether two chronologically sequential measurement values are monotonously rising anti/or monotonously falling. Upon the chronological recording of multiple measurement values, verifying whether their change remains below a specific threshold value is also known.

Erroneous measurement results may sometimes be related to an error in the microcontroller of the analysis instrument. Therefore, many devices are implemented redundantly and comprise two microcontrollers operating in parallel. The use of a second microcontroller (hardware) not only increases the space required in the analysis instrument, it also makes the instrument more expensive. In addition, procedures must be provided for the parallel processing of the measurement signals.

The problem is known in the prior art that the desired concentration value must be concluded from the optically determined measurement values (reflection values). The plausibility check of the concentration values is only performed on the basis of threshold values previously established therein, however.

If the measuring and evaluation device is designed in the form of software, the redundancy may also be provided by a second software module. However, the processing effort is greater, because two programs running in parallel must be executed. In addition, the programming is complex. Determining the analysis result takes longer due to the parallel processing.

It is thus an object of the invention to provide an analysis system for photometric determination of an analyte in a body fluid, which allows a simple verification of the measuring and evaluation device.

SUMMARY

This object and others that will be appreciated by a person of ordinary skill in the art have been achieved according to the embodiments of the present invention disclosed herein. In one embodiment, the object is achieved by a method generally having the features of claim 1. In other embodiments, the object is achieved by an analysis system generally having the features of claim 11. The dependent claims define various other embodiments of the method and analysis system according to the present invention.

The analysis system according to the present invention for photometric determination of an analyte in a body fluid comprises an analysis instrument and a test carrier. The analysis instrument has an evaluation zone, in which a photometrically detectable change occurs as a result of a reaction of a sample of the body fluid, which is contacted with the test carrier, with a reagent which is contained in the test carrier.

The analysis instrument includes an optical emitter for emitting light on to the evaluation zone of the test carrier, an optical receiver for detecting light which is received from the evaluation zone, and for generating a measurement signal corresponding to the received light. The light from the evaluation zone can either be (diffusely) reflected on the evaluation zone or can be transmitted through the evaluation zone before it reaches the optical receiver. The measurement signal generated by the receiver corresponds to the intensity of the received light. The analysis instrument comprises a measuring and evaluation device having a measuring unit and an evaluation unit.

The measurement signal which is received in the optical receiver is amplified and digitized in the measuring unit. The desired concentration value is determined from the digitized measurement signal in the evaluation unit using an evaluation algorithm, which comprises an assignment between values of the measurement signal and concentration values. The assignment between the values of the measurement signal and the concentration values can be stored as a formula, function, or a table.

It has been established in the context of the invention that the analysis instruments sometimes output erroneous measurement results, which cannot be related to a systematic error, however. The occurring errors arise sporadically and are a function of environmental influences, for example a function of the ambient temperature or the ambient conditions, such as humidity or air pressure. It has also been established that the measuring and evaluation device, which is implemented in the form of a microcomputer, of the analysis instruments can deliver erroneous results as a function of the values to be processed, i.e., the measurement signals applied to the input. A chronological occurrence of an error apparently results.

An error of this type may be detected easily if a control value, which is detected in the algorithmic sequence after the execution of a computing step for determining the measurement result, is compared to an expected value. The algorithmic sequence comprises at least one computing step of a processor or microcomputer. In addition, it can also include further algorithmic and/or computing steps, in order to determine the desired measurement result from the values of the measurement signal, for example, a concentration value or a value which represents a concentration. The measurement result could also be an "intermediate value", which is used in the processor for further processing.

According to the embodiments of the present invention, the control value is the concentration value. It is verified using a control algorithm, in which a deviation of the determined control value from an expected value is determined. The expected value is a reference concentration value. If this deviation exceeds a predefined limiting value, an error is recognized in the measuring and evaluation device. At this point, additional knowledge about the value of the control variable is implemented in the system according to the invention. For example, it is known which behavior the control value has and/or in which broad ranges the control value must be. This can be determined by a measuring series in the laboratory or using reference systems, which have redundantly constructed measuring and evaluation devices.

In the context of the invention, the control value is understood generally as a value during the processing of the measurement signal for determining the measurement result and/or the desired concentration value. According to certain embodiments of the present invention, the control value is the desired concentration value itself, so that the verification of the measuring and evaluation device occurs at the end of the determination of the concentration value. The control value can also be formed from other "intermediate values" during the processing of the measurement value, however, for example, from internal-processor computing variables, which represent the concentration, or from processed remission values (intensity of the light reflected from the test carrier).

The control variable is acquired at an acquisition point. This acquisition point is a point in the algorithmic sequence inside the processor, when at least one computing step for determining the concentration value has already been executed. The acquisition point is thus downstream at least one computing step in relation to the algorithmic sequence. It can be, for example, a location in the measuring and evaluation device and/or in the microcomputer or also a sequence point in a computer program if the measuring and evaluation device is implemented in the form of software in a microcomputer, e.g., in an ASIC.

The control value is described hereafter as a concentration value without restriction of the generality. Of course, instead of the concentration value, any other suitable value can also be used as the control value. A reference concentration value is used as the expected value, also without restriction of the generality. The expected value and the control value are typically adapted to one another in such a manner that the control value and the expected value relate to the same variable. In other words: if the control value is a value of the concentration, for example, then the expected value is also a value of the concentration.

The concentration value is monitored according to the invention by means of a control algorithm, in which a deviation of the determined concentration value from a reference concentration value is determined, the reference concentration value can be parameterized as a function of the analyte to be measured, the test carrier, or the determination method for determining the concentration value. For this purpose, general knowledge about the concentration value can be implemented. If the deviation of the concentration value from the reference concentration value exceeds a predefined threshold value, an error is recognized in the measuring and evaluation device.

The evaluation algorithm for determining the desired concentration value from the digitized measurement signal is typically a function of at least the test carrier used. Deviations of different test carriers, which have been produced by various production methods, result in this case.

The term "various production methods" is understood here to mean that different test carriers have been produced on different machines or facilities or, if identical machines and facilities are used, using different methods and/or employing different materials or method durations of individual method steps. For example, test carriers which have been produced using the same method sequence on the same machine at different times and in different production batches could have all of the same information and parameters, which are used in the evaluation algorithm for determining the desired concentration value.

By means of a reference value and a limiting value which can be parameterized simply and precisely, the concentration value determined by the measuring and evaluation device can be monitored rapidly and reliably.

A second exact determination of the concentration value, for example, using a redundant system, is not necessary for verifying the concentration value. Rather, one verification of the concentration value is sufficient. In this case, the determined concentration value is compared to a reference concentration value. For this purpose, a reference assignment is used, which is implemented in the control algorithm. A plurality of reference measurement values is assigned with a plurality of reference concentration values using the reference assignment. To verify a concentration value determined from the current measurement value of the measurement signal, firstly the reference value is selected which is adjacent to the current measurement value of the measurement signal. The corresponding reference concentration value is determined from this reference value by means of the reference assignment. The selected reference concentration value is compared to the determined concentration value, the deviation not being able to exceed a predetermined limiting value. The predetermined threshold value (limiting value) can be parameterized easily.

The evaluation algorithm for determining the desired concentration value from the digitized measurement signal is a function of the test carrier used and is thus specific to the production method, as explained above. Values "specific to the production method" in the meaning of the invention are values which are a function of the production method, which comprises the machines and facilities or the method for production, for example. A change of the method on a specific machine, for example, by changing the materials used, the sequence of method steps, or also the chronological duration of individual method steps results in a change of the values specific to the production method. The production-method-specific values also change if a different machine or facility is used or if an existing machine is changed, but the method remains the same. The totality of stored function and/or relation and the variables defined in such a function, which could be changeable parameters, is understood as the evaluation algorithm. In particular, the variables of the assignment of the concentration values to the values of the measurement signal can be dependent of the test carriers used, the evaluation algorithm comprises the concentration values. The production-method-specific assignment and the evaluation algorithm are thus specific to the production method.

The evaluation algorithm for determining the desired concentration value from the digitized measurement value is typically specific to the production batch (production-batch-specific) or batch-specific. The test carriers which have been produced in different production batches in the same production facility differ, which is to be taken into consideration in the evaluation algorithm.

The assignment of the concentration to the measurement values of the measurement signal values, which is used to determine the concentration value, is typically batch-specific for the production batch of the test carrier used. Before the first use of a test carrier of a new production batch, information about the batch-specific assignment is therefore inputted in the analysis instrument and stored in a memory of the analysis instrument.

As the assignment of the evaluation algorithm is specific to the production method, the reference assignment which is used in the control algorithm and associates a plurality of reference measurement values with a plurality of reference concentration values is a function of the test carrier used for the analysis. The reference assignment is typically specific to the production method. It can also be specific to the production batch.

The reference assignment can also be specific to the production batch, so that the reference assignment must also be stored in the analysis instrument before the first use of a test carrier of a new production batch. The reference assignment can either be inputted in the analysis instrument, i.e., by means of a data carrier, or can be externally transmitted via an interface. The reference assignment is then generated in another device and stored in a memory of the analysis instrument.

The verification of the concentration value by means of a control algorithm, which assigns a reference assignment a plurality of reference concentration values to a plurality of production-method-specific reference measurement values, has the advantage that an exact control, which is adapted and specific to the individual test carriers used, occurs. In this manner, the concentration values determined by the evaluation algorithm of the processor are monitored. As a result, a verification of the processor or microcontroller used takes place, so that sporadically occurring, non-systematic errors of the microprocessor can also be recognized and acquired. The reliability of the analysis system used increases substantially.

Simultaneously, this procedure proves to be particularly simple and efficient, because no second measurement must be performed and no redundant acquisition and evaluation of an optical signal must take place. The analysis system according to the invention is therefore particularly reliable and robust. It is distinguished by rapid processing and low costs.

Alternatively, the reference assignment (association) can particularly preferably be generated in the analysis instrument itself. It is generated via the evaluation algorithm using predetermined reference measurement values, a reference concentration value being assigned with each reference measurement value by application of the assignment stored in the evaluation algorithm. The generated reference assignment is stored in the analysis instrument. For example, the reference assignment can be stored in the form of a "lookup table" or in another tabular form as value pairs. In one embodiment at least 10, and in other embodiments at least 30 value pairs are stored in the reference assignment. In the context of the invention, approximately 50 value pairs have proven to be particularly suitable. The more value pairs are stored, the more precise the verification of the determined concentration value can be.

The storage of the reference assignment must take place before the first use of a test carrier, in particular before the use of a test carrier of a specific production method, because the reference assignment is also a function of the production method. If the reference assignment of the test carriers is a function of a dependence on the production batch, the storage and/or generation of the reference assignment is to be performed before the first use of a test carrier of a new production batch, because the reference assignment can also be a function of the production batch and can deviate for test carriers of different production batches, like the assignment of the evaluation algorithm.

If the reference assignment of the control algorithm is prepared in the analysis instrument by applying of the assignment of the evaluation algorithm, the reference assignment can additionally be verified. The determined reference concentration values are preferably verified for mathematical monotony, i.e., examined as to whether the reference concentration values describe a function and/or a sequence having a slope in the same direction. For this purpose, according to the invention, the knowledge about the concentration values as a function of the emitted light, i.e., the measurement signal, is used. For rising measurement values of the measurement signal, i.e., for a rising intensity of the emitted light signal, it is known that the concentration falls monotonously. Therefore, the reference concentration values must also fall with rising reference measurement values. Of course, it is also possible to verify monotonously rising concentrations. Photometric methods which are based on luminescence also have rising concentration values in the event of rising measurement values. The reference concentration values must also rise with rising reference measurement values here.

The reference assignment generated by application of the assignment of the evaluation algorithm can optionally be verified for "smoothness". The deviations between two sequential reference concentration values cannot be excessively great, in particular, cannot exceed a predetermined tolerance value, which can be parameterized and which can be stored in a memory of the analysis instrument.

Otherwise, an error of the measuring and evaluation device is recognized. An error can now either be outputted or the determination of the reference assignment can be repeated. Deviating reference measurement values may be used upon repeating to determine the reference assignment.

The measuring and evaluation device can also be verified in acquiring a plurality of sequential auxiliary measurement values of the measurement signal in the measuring unit at a plurality of measuring times. The sequential auxiliary measurement values are compared in the measuring and evaluation device to the particular preceding auxiliary measurement values. It is thus examined whether the auxiliary measurement values form a mathematically monotonous function or sequence. The auxiliary measurement values must thus all have a slope in the same direction. If this is not the case, a failure of the measuring and evaluation device is recognized. It is clear to one skilled in the art that this verification can be performed alternatively and/or additionally to the verification of the deviation of the control value from the expected value.

The embodiments of the method according to the invention for determining an analyte in a body fluid, by means of an analysis system having an analysis instrument and a test carrier, generally comprises multiple steps. The method embodiments also achieve the stated object. The optical emitter of the analysis instrument emits light onto the evaluation zone of the test carrier, in which a photometrically detectable change occurs. A corresponding measurement signal is generated from the light of the evaluation zone, which is amplified and digitized in the measuring unit.

Subsequently, the desired concentration value is determined from the digitized measurement signal in the evaluation unit by means of an evaluation algorithm. The evaluation algorithm comprises an assignment specific to the production method between values of the digitized measurement signal and concentration values, at least one computing step being executed by means of a processor in the evaluation algorithm. In the algorithmic sequence down-stream from the execution of the computing step, the concentration value is acquired at an acquisition point in the evaluation unit and verified by a control algorithm. By means of a reference assignment of the control algorithm, a plurality of reference measurement values are each assigned to one of a plurality of reference concentration values. The reference concentration value is determined from a reference measurement value by employing the reference assignment and a deviation between the determined concentration value and the associated reference concentration value is determined. An error of the measuring and evaluation device is recognized if the deviation of the concentration value from the reference concentration value exceeds a predefined threshold value.

The embodiments of the method have the advantage that not only the measuring unit, but rather also the evaluation unit is verified. Errors of the evaluation unit, in particular sporadically occurring errors, may thus be detected. In other words, the processor or microprocessor of the measuring and evaluation device is checked. This check occurs as a function of the test carriers used, information specific to the production method of the test carrier being taken into consideration in the implemented assignment of the evaluation algorithm and in the implemented reference assignment of the control algorithm. The result of the verification is thus very exact and reliable.

The information specific to the production method of the test carrier is typically stored in a memory of the analysis instrument. The information about the assignment specific to the production method is inputted into the memory, before the evaluation algorithm is executed for test carriers of a production method. A reference assignment specific to the production method is also stored in the memory in connection with the input of the information about the evaluation algorithm and before its first use.

In a further embodiment of the method, the production-method-specific assignment is batch-specific, so that upon the use of test carriers of another production batch, the batch-specific information is taken into consideration.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
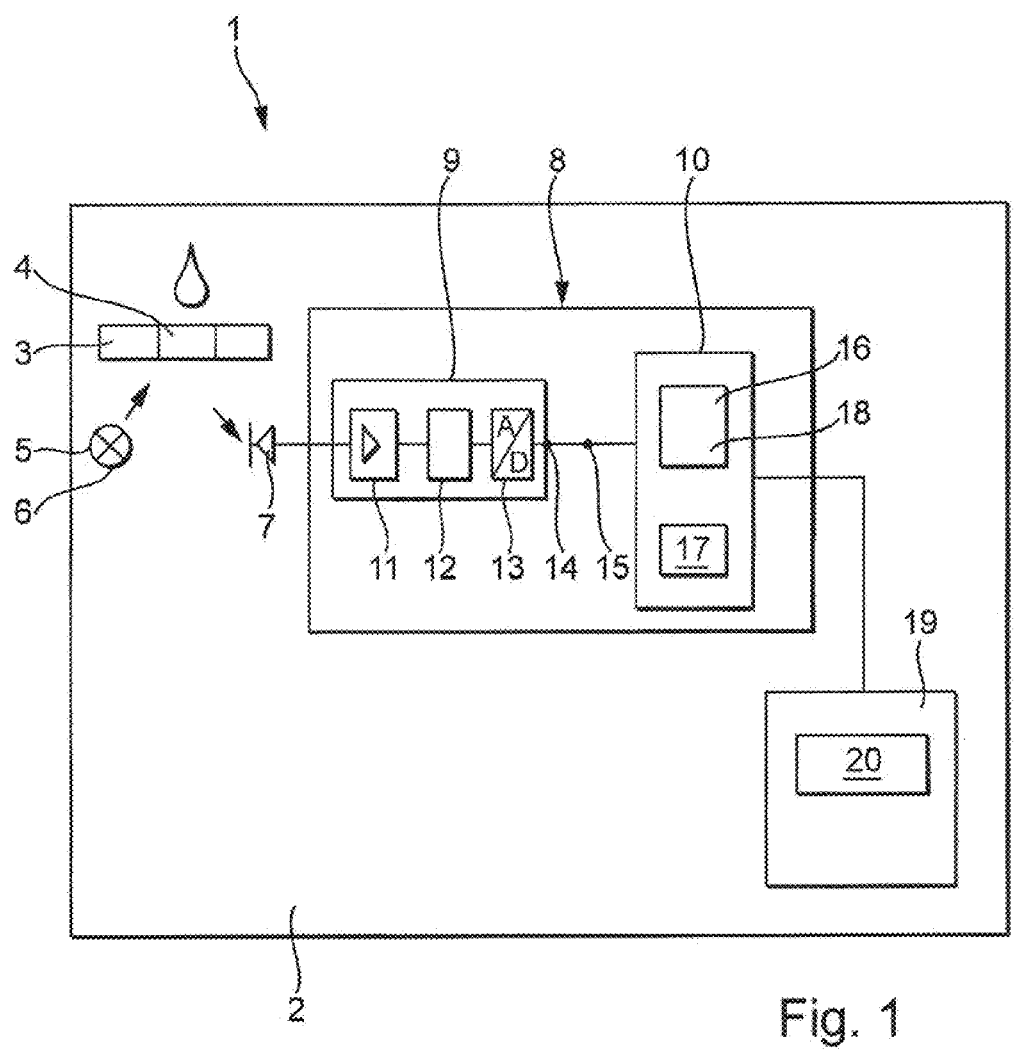
FIG. 1 shows a schematic circuit diagram of an analysis system having an analysis instrument and a test carrier.

FIG. 1 shows an analysis system 1 having an analysis instrument 2 and a test carrier 3, which is implemented as a test strip and has an evaluation zone 4. A reagent is contained in the evaluation zone 4, which causes a reaction, upon the presence of an analyte in a body fluid which is applied to the evaluation zone 4. The change of the reaction is photometrically detectable.

The evaluation zone 4 of the test carrier 3 is irradiated with light by an optical emitter 5. The emitter 5 is implemented as a light source 6, in particular as a light emitting diode. Of course, multiple arbitrary light sources may also be provided, which are connected in parallel or in series. The light emitted by the test carrier 3 is received by an optical receiver 7. The receiver 7 is a light sensor, such as a photodiode 8. The light reflected from the test carrier 3 is referred to as remission. The intensity of the reflected light is measured and converted into a corresponding measurement signal.

The measurement signal, which corresponds to the intensity of the received light, is relayed to a measuring and evaluation device 8, which comprises a measuring unit 9 and an evaluation unit 10. The measuring unit 9 includes an amplifier 11, a measuring circuit 12, which is implemented as a band filter or similar component, and an A/D converter 13. A digitized measurement signal 15, which is referred to as remission, is available at an output 14 of the measuring unit 9.

The digitized measurement signal 15 is processed by the evaluation unit 10. The evaluation unit 10 includes a microcontroller 16 and a memory 17. An assignment is implemented in the microcontroller 16, by means of which a concentration value is determined from the measurement signal 15. The concentration value is checked for its correctness in that it is compared to a reference concentration value and the deviation from a reference concentration value is determined. If the deviation exceeds a predetermined threshold value, an error is recognized.

The recognized error is transmitted to a display unit 19 and displayed on a display 20, for sample. If the determined concentration value is correct, i.e., if the deviation is less than the threshold value, the determined concentration value is displayed on the display 20.

Figure 2:
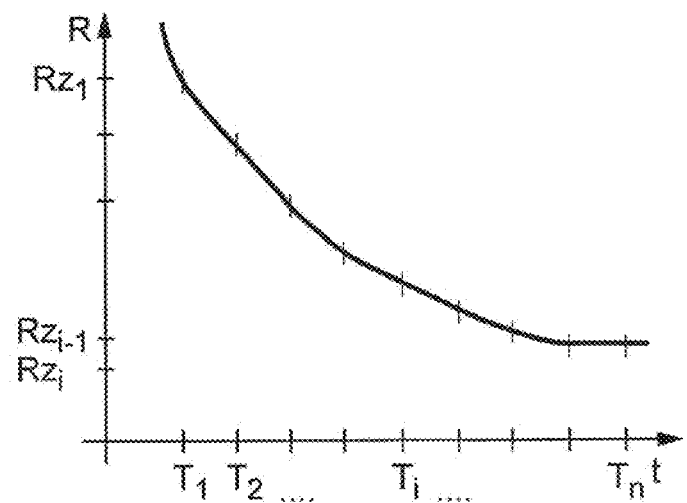
FIG. 2 shows the time curve of the light received by the optical receiver of the analysis instrument over time.

FIG. 2 shows the time curve of the remission (intensity of the light reflected from the test carrier 3) received by the receiver 7. Of course, light transmitted from the test carrier 3 can also be used as the basis for the concentration determination. The remission is the measurement signal which is processed by the measuring unit 9. According to the invention, the measurement signal 15 digitized by the measuring unit 9 can be verified. The known knowledge about the time curve of the remission is used as the basis for this purpose, the time curve can be described by a monotonously falling curve. To verify the measurement signal, a plurality of auxiliary measurement values of the measurement signal is determined at a plurality of measuring times T1, T2, ... Tn, in this embodiment the auxiliary measurement values are designated as intermediate measurement values or intermediate remission values, Rz1, Rz2 ... Rzn, The auxiliary measurement values do not necessarily have to be values which are before the measurement value in time, which was used to ascertain the measurement result. The sequential intermediate measurement values Rzi are compared to the particular preceding measurement value Rzi−1. It is verified whether a mathematically monotonous curve is provided. Using this method, the "quality" of the signal acquisition is already monitored and an error of the measuring and evaluation device resulting from a erroneous measurement is recognized.

To verify for falling monotony, it is determined whether the intermediate measurement value Rzi has a lesser value than the immediately preceding intermediate value Rzi−1. If this is not the case, there is an error in the measuring unit 9. An error signal is outputted. If it is verified whether the intermediate measurement values Rzi form a monotonously rising function, the intermediate measurement value Rzi must be greater than the immediately preceding intermediate measurement value Rzi−1. Alternatively, the absolute value of the deviation between two sequential intermediate values can also be determined. This is sufficient if only unacceptable deviations of the intermediate measurement values, so-called spikes, are to be recognized early.

To determine the concentration value, the value of the measurement signal (remission value), i.e., the intermediate measurement value Rzi, can be used, which deviates from the preceding intermediate measurement value Rzi−1 by less than a predetermined threshold value. This threshold value can be parameterized easily. It is thus ensured that the "correct" intermediate measurement value is used as the current measurement value of the measurement signal for the determination of the concentration value. This is the case if the chronological change of the measurement value (remission value) is negligible.

Figure 3:
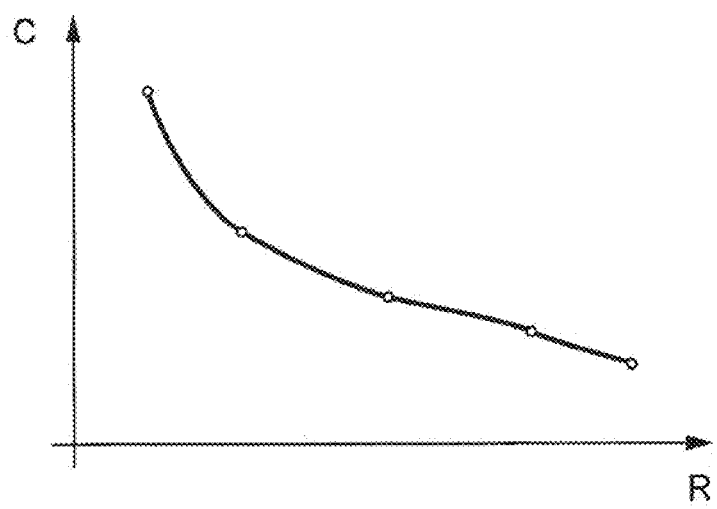
FIG. 3 shows an assignment between the measurement values of a measurement signal and the concentration values for a test carrier.

FIG. 3 shows the assignment of the values of the measurement signal R, i.e., the remission measuring values, to the concentration values C. The assignment can be stored in the form of a table or a function and/or a curve. The assignment of the evaluation algorithm can be approximated by a spline function. A spline function having at most ten support points has proven to be suitable, and an approximation by a spline function having at most five support points is typical. For example, the spline function may be formed by a third-degree function. The parameters for describing the third-degree function are each a function of the production batch of the test carrier 3 used and are each inputted into the analysis instrument before the first use of a test carrier of a new production batch, this information (parameters) being stored in the memory 17 of the analysis instrument 2. Upon an approximation of the assignment for a third-degree spline function at five support points, a total of sixteen parameters must be stored.

Figures 4A, 4B:
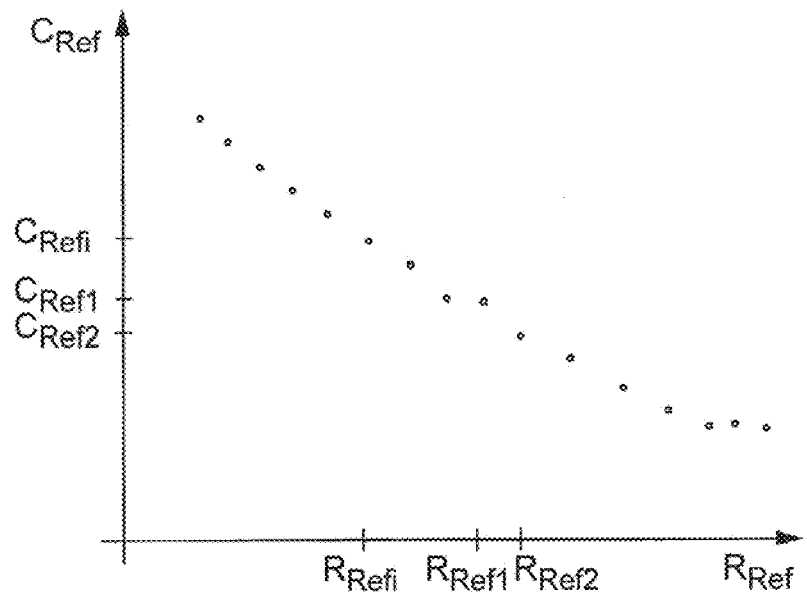
FIGS. 4a and 4b show different illustrations of a reference assignment of the analysis instrument.

Before the first use of a test carrier 3 of a new production batch, after the input of the information about the batch-specific assignment, a reference assignment is prepared. A reference assignment of this type of reference measurement value RRef1 (reference remission values) to reference concentration values CRef is shown in FIG. 4a. A plurality of predetermined reference measurement values is applied to the assignment of the evaluation algorithm. A reference concentration value CRefi is thus prepared for each reference measurement value RRefi. The reference assignment can be produced for at least thirty, and even as much as at least fifty reference measurement values. The reference assignment between reference measurement values RRef and reference concentration values CRef can also be stored in the form of a "lookup table" as shown in FIG. 4b.

In order to verify the determined concentration value which was determined from the current measurement value of the measurement signal, the reference measurement value (RRefi) matching the current measurement value is determined. The reference concentration value CRefi for this reference measurement value (RRefi) is determined using the reference assignment. The selected reference concentration value is compared to the determined concentration value.

For example, the reference measurement value (RRefi), which is adjacent to the current measurement value of the measurement signal, can be selected from the reference assignment. The direct vicinity is not important. It is also possible that a reference measurement value (RRefi) is selected which is a pre-determined number of reference measurement values away from the current measurement value of the measurement signal. For example, three or five further reference measurement values may be between the selected reference measurement value (RRefi) and the current measurement value of the measurement signal.

However, the directly adjacent reference measurement value (RRefi), which is closest to the current measurement value of the measurement signal, can also be selected.

Alternatively or optionally, a first and a second reference concentration value CRef1, CRef2 are determined from a first and a second reference measurement value RRef1, RRef2. The values which are each adjacent to the current measurement value of the measurement signal or are a predetermined number of reference measurement values away from it are selected as the first and the second reference measurement values RRef1, RRef2. The determination of the two reference concentration values CRef1, CRef2 is performed by means of the reference assignment. The determined concentration value is then verified via the control algorithm using the first and the second reference concentration values CRef1, CRef2. The measured concentration value should be between the first and the second reference concentration values CRef1, CRef2.

An error of the measuring and evaluation device 8 is recognized if the determined concentration value is not between the first and the second reference concentration values CRef1, CRef2, i.e., if the determined concentration value is greater than the first reference concentration value CRef1 and less than the second reference concentration value CRef2.

Alternatively, the threshold value, which is used as the basis for verifying the deviation of the concentration value from only one reference concentration value, can be determined from the difference of the first and second reference concentration values CRef1, CRef2.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. An analysis system for the photometric determination of an analyte in a body fluid, the system comprising an analysis instrument and a test carrier, the test carrier comprising an evaluation zone in which a photometrically detectable change occurs as a result of a reaction of a sample of the body fluid contacted to the test carrier with a reagent contained in the test carrier, the analysis instrument comprising:
   an optical emitter for emitting light onto the evaluation zone of the test carrier;
   an optical receiver for receiving light from the evaluation zone and for generating a measurement signal corresponding to the received light;
   a measuring and evaluation device having a measuring unit and an evaluation unit, wherein
      the measuring unit is capable and adapted for amplifying and digitizing the measurement signal generated by the receiver,
      the evaluation unit is capable and adapted for determining the desired concentration value from the digitized measurement signal using an evaluation algorithm, which comprises a production-method-specific assignment of concentration values to the values of the digitized measurement signal, wherein in the evaluation algorithm at least one computing step is executed by means of a processor,
      the evaluation unit is capable and adapted for acquiring in the algorithmic sequence of steps the concentration value at an acquisition point downstream from the execution of the computing step,
   and wherein the concentration value is verified by means of a control algorithm by determining a deviation of the determined concentration value from a reference concentration value, the reference concentration value being determined from a reference measurement value using reference assignment data in the control algorithm, the reference assignment data assigning a plurality of reference concentration values to a plurality of reference measurement values,
   and wherein the analysis system is capable and adapted for recognizing an error of the measuring and evaluation device if the deviation of the concentration value from the reference concentration value exceeds a predefined limiting value.

2. The analysis system according to claim 1, wherein the analysis instrument comprises a memory in which information specific to the production method of the test carrier is stored and information about the production-method-specific assignment is inputted into the memory before the evaluation algorithm is executed for a test carrier, and the reference assignment is stored in connection with the storing of production-method-specific information about a new production-method-specific evaluation algorithm and before the first use thereof.

3. The analysis system according to claim 1, wherein the production-method-specific assignment between values of the digitized measurement signal and concentration values is specific to the production batch, and information about the production-batch-specific assignment is inputted into a memory before an evaluation algorithm is executed for a test carrier of a new production batch, and wherein, in connection with the input of the information about a new production-batch-specific evaluation algorithm and before the first use thereof for a test carrier of a new production batch, a specific reference assignment is stored.

4. The analysis system according to claim 1, wherein the reference concentration value is determined from a reference measurement value which is adjacent to the current measurement value of the measurement signal, using the reference assignment data.

5. The analysis system according to claim 1, wherein the reference concentration value is determined from a reference measurement value which is a specific number of reference measurement values away from the current measurement value of the measurement signal, using the reference assignment data.

6. The analysis system according to claim 1, wherein using the reference assignment, a first and second reference concentration value (ERef1, ERef2) are determined from a first and second reference measurement value (RRef1, RRef2), which are adjacent to, or a predetermined number of reference measurement values away from the current measurement value of the measurement signal, and the concentration value is verified using the first and the second reference concentration values (ERef1, ERef2) by means of the control algorithm.

7. The analysis system according to claim 6, wherein an error of the measuring and evaluation device is recognized if the concentration value is one of more than the first reference concentration value (ERef1) and less than the second reference concentration value (ERef2).

8. The analysis system according to claim 1, wherein the reference assignment is generated by means of the evaluation algorithm using predetermined reference measurement values.

9. The analysis system according to claim 1, wherein the reference concentration values of the reference assignment of the control algorithm are examined for mathematical monotony.

10. The analysis system according to claim 1, wherein the assignment of the evaluation algorithm is approximated by a spline function having at most about 10 support points.

11. A method for the photometric determination of an analyte in a body fluid using an analysis system comprising an analysis instrument and a test carrier, the test carrier having an evaluation zone, in which a photometrically detectable change occurs as a result of a reaction of a sample of the body fluid contacted with the test carrier with a reagent contained in the test carrier, and the analysis instrument comprising an optical emitter for emitting light, an optical receiver for receiving light, a measuring and evaluation device having a measuring unit and an evaluation unit, the method comprising the following steps:
 a) emitting light from the emitter onto the evaluation zone of the test carrier;
 b) receiving light from the evaluation zone;
 c) generating a measurement signal corresponding to the received light;
 d) amplifying and digitizing in the measuring unit the measurement signal generated by the receiver;
 e) determining in the analysis unit the desired concentration value from the digitized measurement signal using an evaluation algorithm which comprises an assignment between values of the digitized measurement signal and concentration values, the assignment being specific to the production method, at least one computing step being executed by a processor in the evaluation algorithm,
 f) acquiring the concentration value in the evaluation unit at an acquisition point in the algorithmic sequence of steps downstream from the execution of the computing step;
 g) verifying the concentration value using a control algorithm by
  g1) assigning a plurality of reference measurement values to a plurality of reference concentration values using a reference assignment;
  g2) determining the reference concentration value using the reference assignment from a reference measurement value;
  g3) using the reference assignment in the control algorithm; and
  g4) determining a deviation of the determined concentration value from the reference concentration value using the reference assignment; and
 h) recognizing an error of the measuring and evaluation device if the deviation of the concentration value from the reference concentration value exceeds a predefined limiting value.

12. The method according to claim 11, in which the analysis instrument comprises a memory in which information of the test carrier is stored, the information being specific to the production method, further comprising the steps of:
 i) inputting information about the production-method-specific assignment before the evaluation algorithm for a test carrier is executed; and
 j) storing the reference assignment in the memory in connection with the input of the information about the production-method-specific evaluation algorithm and before the first use thereof.

13. The method according to claim 12, wherein the production-method-specific assignment between the values of the digitized measurement signal and the concentration values for determining the desired concentration value from the digitized measurement signal is specific to the production batch.

14. The method according to claim 12, further comprising the step of determining the reference concentration value using the reference assignment from the reference measurement value which is adjacent to or a specific number of reference measurement values away from the current measurement value of the measurement signal.

15. The method according to claim 12, further comprising the steps of:
 k) determining a first and second reference concentration value (ERef1, ERef2) using the reference assignment, from a first and second reference measurement value (RRef1, RRef2), which are adjacent to or a predetermined number of reference measurement values (RRef1) away from the current measurement value; and
 l) verifying the concentration value by means of the control algorithm using the first and second reference concentration values (ERef1, ERef2).

16. The method according to claim 12, further comprising the step of recognizing an error of the measuring and evaluation device, if the concentration is one of more than the first reference concentration value (ERef1) and less than the second reference concentration value (ERef2).

* * * * *